US012688930B2

(12) United States Patent
Bonaric et al.

(10) Patent No.: US 12,688,930 B2
(45) Date of Patent: Jul. 21, 2026

(54) MODULAR MEDICAL DEVICE PLATFORM

(71) Applicant: Orthosoft ULC, Montreal (CA)

(72) Inventors: Patrice Bonaric, St Georges d'orques (FR); Francisco Molina, Montpellier (FR); Amandine Geurts, Montpellier (FR)

(73) Assignee: Orthosoft ULC, Montreal (CA)

( * ) Notice: Subject to any disclaimer, the term of this patent is extended or adjusted under 35 U.S.C. 154(b) by 368 days.

(21) Appl. No.: 18/222,837

(22) Filed: Jul. 17, 2023

(65) Prior Publication Data

US 2024/0038378 A1 Feb. 1, 2024

Related U.S. Application Data

(60) Provisional application No. 63/393,214, filed on Jul. 28, 2022.

(51) Int. Cl.
| | |
|---|---|
| *G16H 40/40* | (2018.01) |
| *A61B 50/36* | (2016.01) |
| *H05K 7/14* | (2006.01) |

(52) U.S. Cl.
CPC ............. *G16H 40/40* (2018.01); *A61B 50/36* (2016.02); *H05K 7/14* (2013.01)

(58) Field of Classification Search
CPC ....... A47B 88/00; A47B 88/407; A47B 88/90; H05K 5/00; H05K 5/0256; H05K 7/1492; G16H 40/40; G16H 40/60; A61B 34/35; A61B 50/13; A61B 50/22; A61B 50/24; A61B 50/26; A61B 2050/105; A61B 2050/185; E05B 65/46; E05B 65/462; E05B 65/468; H01R 13/6275; H01R 13/62905; H01R 13/62911; E05C 3/00; E05C 3/002; E05C 3/006; E05C 3/008; E05C 3/02; E05C 3/04; E05C 3/047; E05C 3/048
USPC ...... 312/215, 222, 209, 223.1, 223.2, 223.3, 312/223.6, 286, 333; 361/608, 724, 725, 361/726, 727, 728, 729, 788
See application file for complete search history.

(56) References Cited

U.S. PATENT DOCUMENTS

| | | |
|---|---|---|
| 5,883,757 A | 3/1999 | Hanson |
| 6,271,604 B1 | 8/2001 | Frank, Jr. et al. |

(Continued)

OTHER PUBLICATIONS

"European Application Serial No. 23188239.0, Extended European Search Report mailed Dec. 13, 2023", 9 pgs.

(Continued)

*Primary Examiner* — Daniel J Troy
*Assistant Examiner* — Elizabeth Irene Artalejo
(74) *Attorney, Agent, or Firm* — Schwegman Lundberg & Woessner, P.A.

(57) ABSTRACT

A modular medical device platform can include a chassis forming a plurality of rack bays each including a pair of drawer slides, a plurality of controller modules each including a drawer enclosure including flanges couplable to the pair of drawer slides with the rack bay of the plurality of rack bays, and a plurality of module locks affixed to the chassis and aligned with each rack bay of the plurality of rack bays. Each module lock of the plurality of module locks can include an electrical connector and a locking mechanism adapted to automatically lock a controller module of the plurality of controller modules as the controller module is slid into the rack bay on the pair of drawer slides.

11 Claims, 7 Drawing Sheets

(56)          References Cited

U.S. PATENT DOCUMENTS

| 11,543,856 | B1 * | 1/2023 | Parsian | G06F 1/1607 |
| 12,318,152 | B2 * | 6/2025 | Wiener | A61B 34/35 |
| 2008/0079340 | A1 * | 4/2008 | Adducci | H04Q 1/026 |
| | | | | 312/286 |
| 2011/0196538 | A1 * | 8/2011 | Michael | A61B 50/18 |
| | | | | 700/275 |
| 2012/0120587 | A1 | 5/2012 | Bhutani et al. | |
| 2015/0135783 | A1 | 5/2015 | Jiang et al. | |
| 2019/0201158 | A1 | 7/2019 | Shelton, IV et al. | |
| 2022/0117681 | A1 | 4/2022 | Crawford et al. | |

OTHER PUBLICATIONS

"European Application Serial No. 23188239.0, Response Filed Jul. 23, 2024 to Extended European Search Report mailed Dec. 13, 2023", 15 pgs.

* cited by examiner

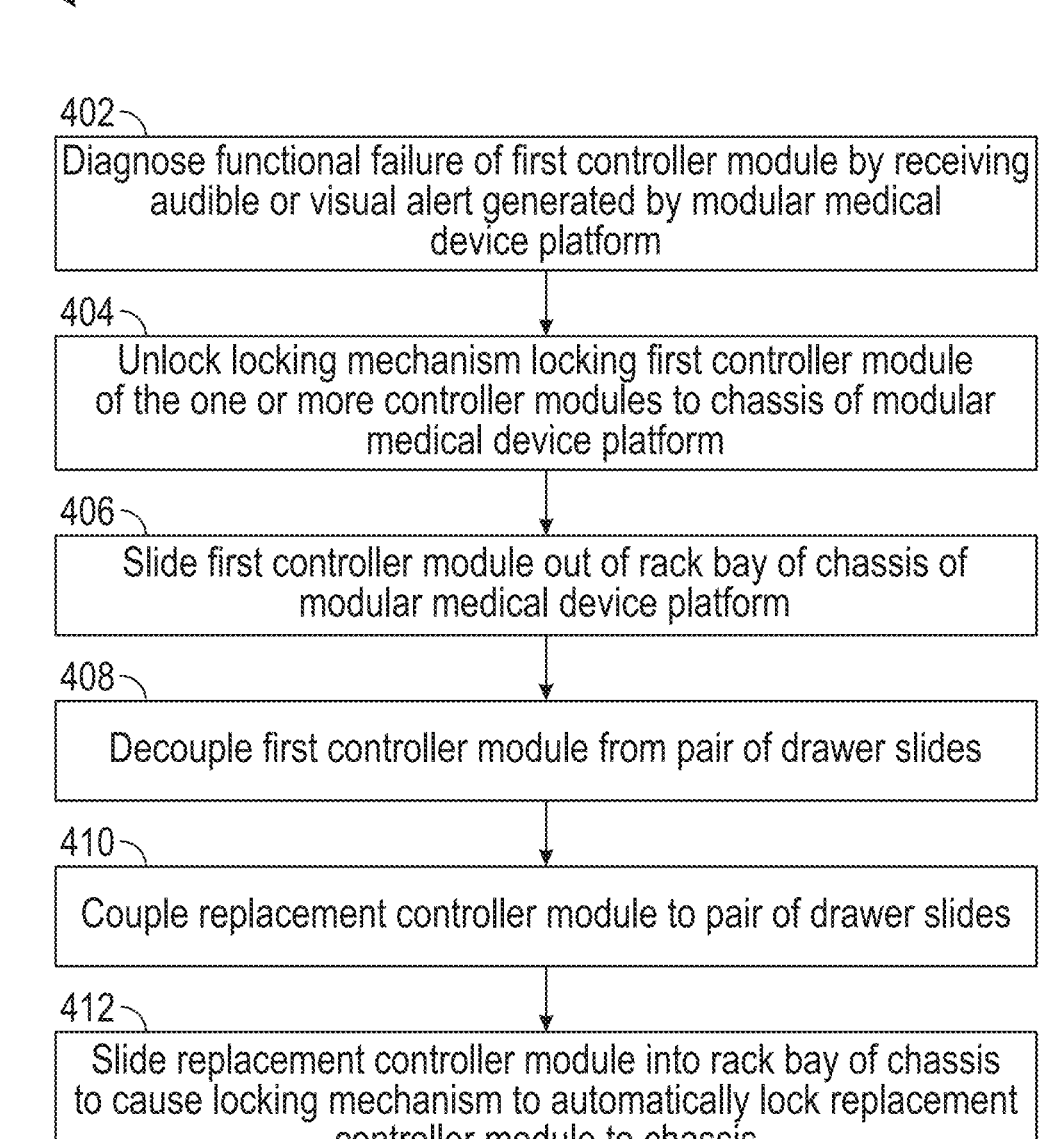

400

402
Diagnose functional failure of first controller module by receiving audible or visual alert generated by modular medical device platform 404
Unlock locking mechanism locking first controller module of the one or more controller modules to chassis of modular medical device platform 406
Slide first controller module out of rack bay of chassis of modular medical device platform 408
Decouple first controller module from pair of drawer slides 410
Couple replacement controller module to pair of drawer slides 412
Slide replacement controller module into rack bay of chassis to cause locking mechanism to automatically lock replacement controller module to chassis

FIG. 6

MODULAR MEDICAL DEVICE PLATFORM

CLAIM OF PRIORITY

This application claims the benefit of U.S. Provisional Patent Application Ser. No. 63/393,214, filed on Jul. 28, 2022, the benefit of priority of which is claimed hereby, and which is incorporated by reference herein in its entirety.

TECHNICAL FIELD

This document pertains generally, but not by way of limitation, to medical devices. More particularly, but not by way of limitation, this document pertains to robotic medical devices and systems for performing robotic surgeries.

BACKGROUND

Various systems exist for controlling or supporting robotic medical devices during robotic surgeries. However, existing systems include several shortcomings. First, for example, many robotic medical devices group the electronic components necessary to enable various functions into an integral control module, which can require all, or the majority of, the electronic components to be removed, inspected, or replaced, such as in the event of a functional failure of power, memory, processing, or networking electronic components. This can increase the cost and complexity of maintaining such robotic medical devices by necessitating removal, and possible replacement, of various electronic components not associated with the functional failure.

Second, the inherent complexity of integral control modules can make repair or refurbishment of such control modules a difficult or time-consuming operation, which can further increase the cost of maintaining such robotic medical devices. Third, many robotic medical devices include one or more control modules secured to a support structure with time-consuming fastening means, such as plurality of bolts, or one or more control modules located within the support, structure in relatively inaccessible locations, both of which can increase the amount of time required to maintain such robotic medical devices. Further, if a functional failure occurs during a surgical procedure, the process of replacing one or more controller modules can significantly extend the length of the surgical procedure, which can lead to decreased end-user satisfaction.

OVERVIEW/SUMMARY

The present disclosure can help to address the above issues, among others, such as by providing a modular medical device platform. The modular medical device platform can include a plurality of controller modules each configured to implement different functions of the modular medical device platform. Each controller module of the plurality of controller modules can include a module connector; and a chassis of the modular medical device platform can include a plurality of module locks each adapted to lock the module connectors of the plurality of controller modules to the chassis within a plurality of rack bays formed by the chassis. For example, a module lock can include a first electrical connector configured to interface with a second electrical connector of a module connector of a controller module to establish power or communication connectivity therebetween, and a locking mechanism adapted to automatically lock the module lock to the module connector of the controller module when the controller module is slid into a rack bay of the chassis. Additionally, each module lock can include a lock handle assembly pivotable to cause the module lock to unlock a module connector of a controller module.

In view of the above, the modular medical device platform can provide a number of benefits over existing robotic medical devices. First, the plurality of controller modules can enable convenient identification and targeted replacement of only the electronic components associated with a functional failure of a robotic medical device platform. For example, the plurality of controller modules can include an electrical power module, a data management module, a communication management module, and a display module each positioned within separate drawer enclosures of the modular medical device platform.

Second, the plurality of controller modules can reduce the development, support, and production costs of a robotic medical device platform. For example, as each controller module of the modular medical device platform can enable different functions of the modular medical device platform, existing functions can be refined, existing issues can be addressed, or various new functions can be introduced, by updating or replacing a single controller module of the plurality of controller modules. Additionally, the division of electrical components into two or more controller modules can help to simplify production workflows to reduce labor costs, such as by enabling one or more of the controller modules to be useable within a variety of different robotic medical devices of a product line or range.

Third, the plurality of module locks and the module connector of each controller module can greatly reduce the amount of time required to replace one or more control modules of a robotic medical device. For example, to remove a controller module of the plurality of controller modules, a user can simply depress the lock handle assembly of a lock module coupling the controller module to the chassis and slide the controller module out of rack bay of the chassis on pair of drawer slides. Subsequently, to replace the controller module, a user can slide a replacement controller module into the chassis on the pair of drawers slides to cause the module lock to automatically lock the controller module to the chassis as the controller module is slid into the rack bay. Therefore, the modular medical device platform can allow a user to rapidly replace one or more control modules of a robotic medical device without using any tools, such as screwdrivers or wrenches, or otherwise removing or engaging with any fasteners securing a control module to the robotic medical device.

A modular medical device platform can comprise: a chassis including a plurality of rack bays, each rack bay of the plurality of rack bays including a pair of drawer slides mounted on opposing sides of the rack bay, the chassis configured to support a medical robot device; a plurality of controller modules, each controller module of the plurality of controller modules including a drawer enclosure including flanges couplable to the pair of drawer slides; and a plurality of module locks affixed to an internal frame of the chassis and aligned with each rack bay of the plurality of rack bays, each module lock of the plurality of module locks including a first electrical connector and a locking mechanism, the locking mechanism including a cam lock adapted to automatically lock a controller module of the plurality of controller modules as the controller module is slid into the rack bay on the pair of drawer slides.

A modular medical device platform can comprise: a chassis to support the medical device, the chassis including an internal support structure comprising a plurality of rack bays; a controller module including a drawer enclosure mountable on drawer slides affixed within a rack bay of the plurality of rack bays, the controller module further including a module connector extending from a back surface of the drawer enclosure; and a module lock affixed on a back portion of the rack bay of the plurality of rack bays, the module lock including a first electrical connector and a cam lock that interfaces with the module connector to electrically couple the controller module to a wiring harness within the chassis and to lock the controller module into the rack bay.

A method of replacing one or more controller modules of a modular medical device platform can comprise: unlocking a locking mechanism locking a first controller module of the one or more controller modules to a chassis of the modular medical device platform; sliding the first controller module out of a rack bay of the chassis of the modular medical device platform; decoupling the first controller module from a pair of drawer slides; coupling a replacement controller module to the pair of drawer slides; and sliding the replacement controller module into the rack bay of the chassis to cause the locking mechanism to automatically lock the replacement controller module to the chassis.

This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

FIG. 6 illustrates a method of replacing one or more controller modules of a modular medical device platform.

Figures 1A, 1B:
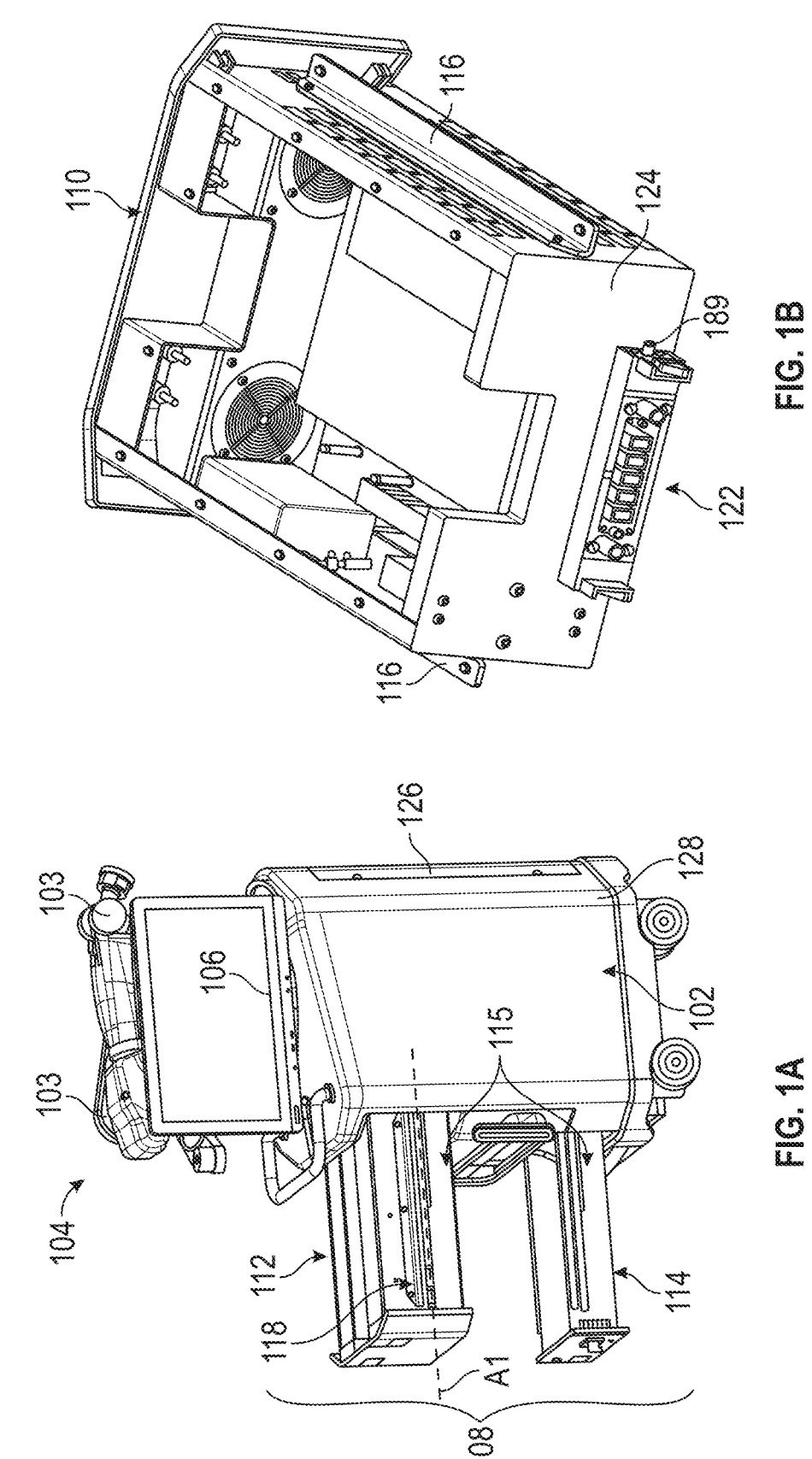
FIG. 1A illustrates an isometric side view of an example modular medical device platform.
FIG. 1B illustrates an isometric rear view of a controller module.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1A illustrates an isometric side view of an example modular medical device platform 100. FIG. 1B illustrates an isometric rear view of an example controller module. FIGS. 1A-1B are discussed below concurrently. The modular medical device platform 100 can include a chassis 102 (FIG. 1A). The chassis 102 can generally be a structure adapted to support a variety of medical robotic devices. In one non-limiting example, such as shown in FIG. 1A, the chassis 102 can be configured to support a robotic arm 104. The robotic arm 104 can include two or more articulating joints 103 (FIG. 1A) capable of pivoting or rotating to provide a user with a wide range of adjustment options. In one non-limiting example, the robotic arm 104 can be a 6 degree-of-freedom (DOF) robot arm, such as the ROSA® robot from Medtech, a Zimmer Biomet Holdings, Inc. company.

The robotic arm 104 can be controlled—with a control system that is processor-implemented based on machine-readable instructions, which when implemented, can cause the robotic arm 104 to move automatically or to provide force assistance to user-guided movement to guide the robotic arm 104. The control system can be realized by a plurality of controller modules 108 (FIG. 1A) in electrical communication with various electronic components of the modular medical device platform 100. A user can also view anatomical imaging, such as displayed on a display screen 106 (FIG. 1A) of the chassis 102, to help guide and position the robotic arm 104. Anatomical imaging can be provided to the display screen 106 with various imaging sources, such as with one or more cameras positioned on an end effector of the robotic arm 104, or intraoperative fluoroscopy, such as with a C-arm.

The plurality of controller modules 108 can include, but is not limited to, one, two, three, four, or five separate controller modules. Each controller module of the plurality of controller modules 108 can include a drawer enclosure 110, such as shown in FIG. 1B. The drawer enclosure 110 can be a housing containing various electronic components, such as any of, but not limited to, a computer system, a power supply, processing circuitry, an ethernet hub, a controller, or other custom or commercially available parts. The electronic components of the modular medical device platform 100 can be distributed amongst the plurality of controller modules 108 by functional theme, such as to enable each controller module of the plurality of controller modules 108 to enable different functions, relative to one another, of the modular medical device platform 100. For example, a first controller module 112 (FIG. 1A) of the plurality of controller modules 108 can be an electrical power module or a data management module, and a second controller module 114 (FIG. 1A) can be a communication management module or a display module.

In one non-limiting example, one or more controller modules of the plurality of controller modules 108 can be adapted to enable functions used during of one type of surgical procedure. For example, the one or more controller modules can include all of the electronic components necessary to enable such functions independently of other controller modules of the plurality of controller modules 108 to enable a user to configure the modular medical device platform 100 for a different type of surgical procedure by replacing the one or more controller modules with one or more controller modules adapted to enable functions used during a different type of surgical procedure. In a further non-limiting example, each controller module of the plurality of controller modules 108 can be adapted to enable functions used during one type of surgical procedure. For example, the first controller module 112 can include all of the electronic components necessary to enable functions used during one type of surgical procedure, and the second controller module 114 can include all of the electronic components necessary to enable functions used during a different surgical procedure.

The chassis 102 can define a plurality of rack bays 115 (FIG. 1A) adapted to support the plurality of controller modules 108. For example, each rack bay of the plurality of rack bays 115 can be sized and shaped to receive the drawer enclosure 110 of each controller module of the plurality of controller modules 108. The plurality of controller modules 108 can be adapted to slid in, or out of, the plurality of rack bays 115. For example, the drawer enclosure 110 of each controller module of the plurality of controller modules 108 can include a pair of flanges 116 (FIG. 1B) mountable to a pair of drawer slides 118 (FIG. 1A) of a plurality of drawer slides. The pair of drawer slides 118 of the plurality of drawer slides can be affixed to opposing surfaces of each rack bay of the plurality of rack bays 115. The pair of flanges 116 can extend laterally outward from opposing surfaces of the drawer enclosure 110 to engage the pair of drawer slides 118. Each pair of flanges 116 and each pair of drawer slides 118 can be coupled to one another, or to the drawer enclosure 110 or the chassis 102, respectively, with various fastening means such as, but not limited to, one or more screws, bolts, rivets, or welds. Each controller module of the plurality of controller modules 108 can thereby be slid into, or out of, a corresponding rack bay of the plurality of rack bays 115 via translation along a longitudinal axis A1 (FIG. 1A) extending parallel to the pair of flanges 116 and the pair of drawer slides 118.

The modular medical device platform 100 can include a plurality of module locks. For example, a module lock 120 (FIG. 2A) can be coupled to the chassis 102 within each rack bay of the plurality of rack bays 115. The drawer enclosure 110 of each controller module of the plurality of controller modules 108 can include a module connector 122 extending outwardly from a back surface 124 thereof. The module lock 120 and the module connector 122 can enable each controller module of the plurality of controller modules 108 to be automatically locked to the chassis 102 when each controller module is received within a corresponding rack bay of the plurality of rack bays 115. For example, a cam lock of the module lock 120 can enter a lock channel of the module connector 122 during translation, along the longitudinal axis A1, of the drawer enclosure 110 into a rack bay of the plurality of rack bays 115.

The module lock 120 and the module connector 122 can also establish electrical power or communication connectivity between the plurality of controller modules 108 and other electrical components of the modular medical device platform 100, as further discussed below with reference to FIGS. 2A-2B. The chassis 102 can also include an access door 126. The access door 126 can be, for example, but not limited to, a hinged door located along a back surface 128 of the chassis 102. The access door 126 can enable a user to access various electrical components, such as a wiring harness 137 (FIG. 5), located within the chassis 102; and to unlock one or more of the module locks 120 from the module connectors 122 when the plurality of controller modules 108 are received within the plurality of rack bays 115. The access door 126 can also include a lock, such as to help prevent unauthorized or untrained users from accessing internal electronic components of the modular medical device platform 100.

Figure 2B:
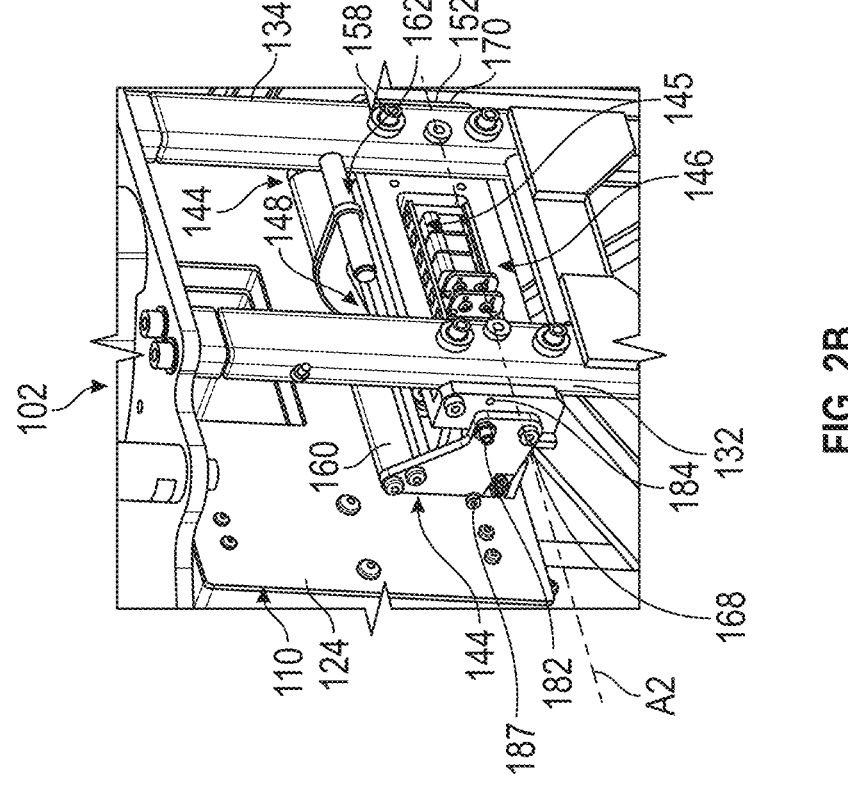
FIG. 2B illustrates a rear isometric view of a module lock coupled to a module connector of a drawer enclosure.
Figure 2A:
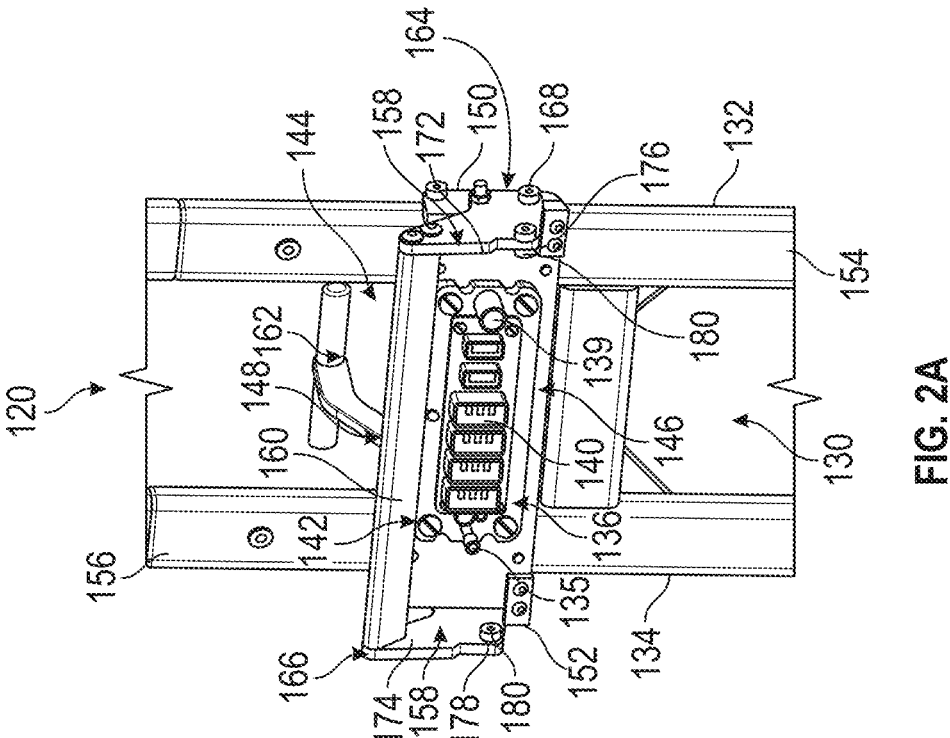
FIG. 2A illustrates a front isometric view of a module lock.
Figure 2C:
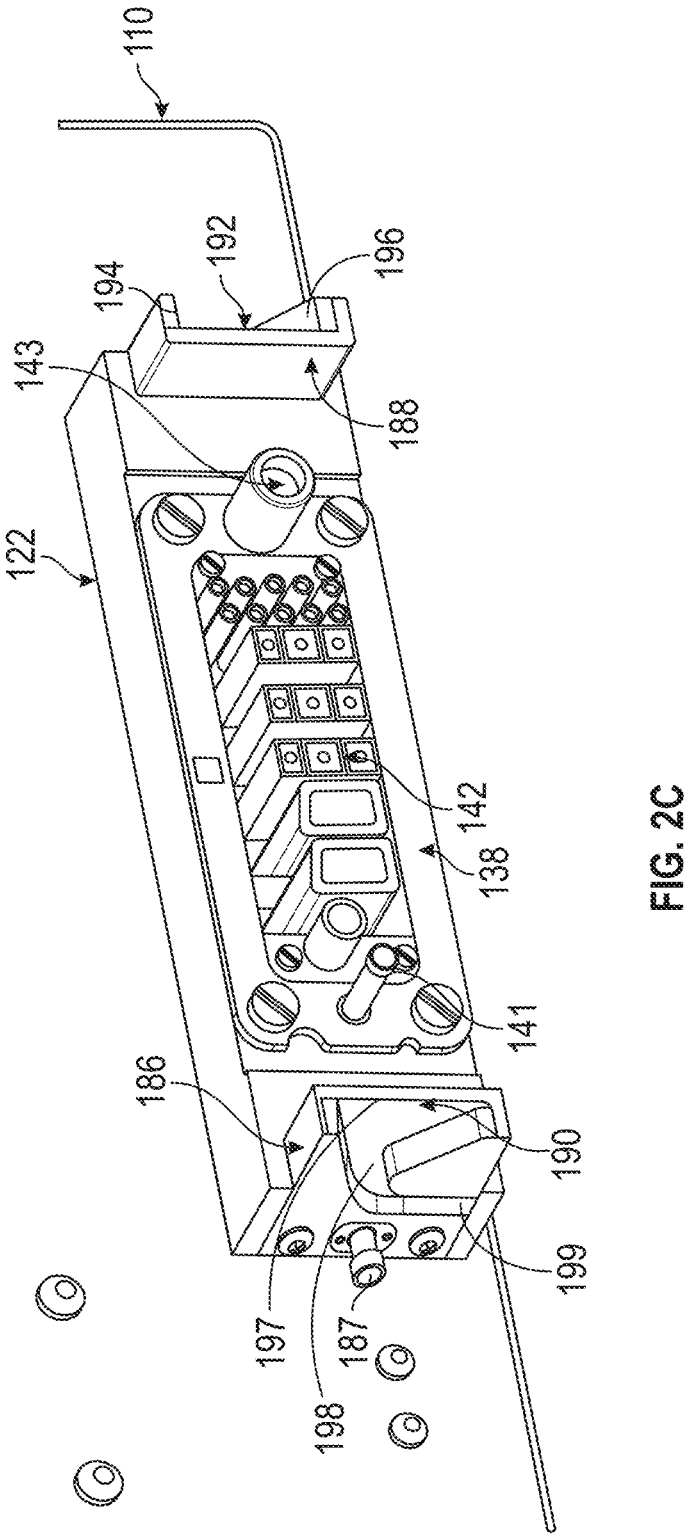
FIG. 2C illustrates a front isometric view of a module connector of a drawer enclosure.

FIG. 2A illustrates a front isometric view of a module lock 120. FIG. 2B illustrates rear isometric view of a module lock 120 coupled to a module connector 122 of a drawer enclosure 110. FIG. 2C illustrates a front isometric view of a module connector 122 of drawer enclosure 110. FIGS. 2A-2C are discussed below concurrently. The chassis 102 (FIG. 2B) can include an internal frame 130. The internal frame 130 can be an internal framework configured to support and position any of various components of the modular medical device platform 100 (FIG. 1A). The internal frame 130 can form the plurality of rack bays 115 (FIG. 1A).

The internal frame 130 can include a first vertical support member 132 (FIG. 2A) and a second vertical support member 134 (FIG. 2A). The first vertical support member 132 and the second vertical support member 134 can extend within the chassis 102 near, or otherwise proximal to, the back surface 128 (FIG. 2B). For example, the first vertical support member 132 and the second vertical support member 134 can be visible and easily accessible to a user when the access door 126 (FIG. 1A) is open. The first vertical support member 132 and the second vertical support member 134 can support a plurality of module locks within the chassis 102. For example, the module lock 120 can be a first, second, third, fourth, or fifth module lock, and the module lock 120 can be coupled to the first vertical support member 132 and the second vertical support member 134 in a position aligning the module lock 120 (FIGS. 2A-2B) with the module connector 122 (FIGS. 2B-2C) of a first, second, third, fourth, or fifth controller module received within a rack bay of the plurality of rack bays 115.

Figure 5:
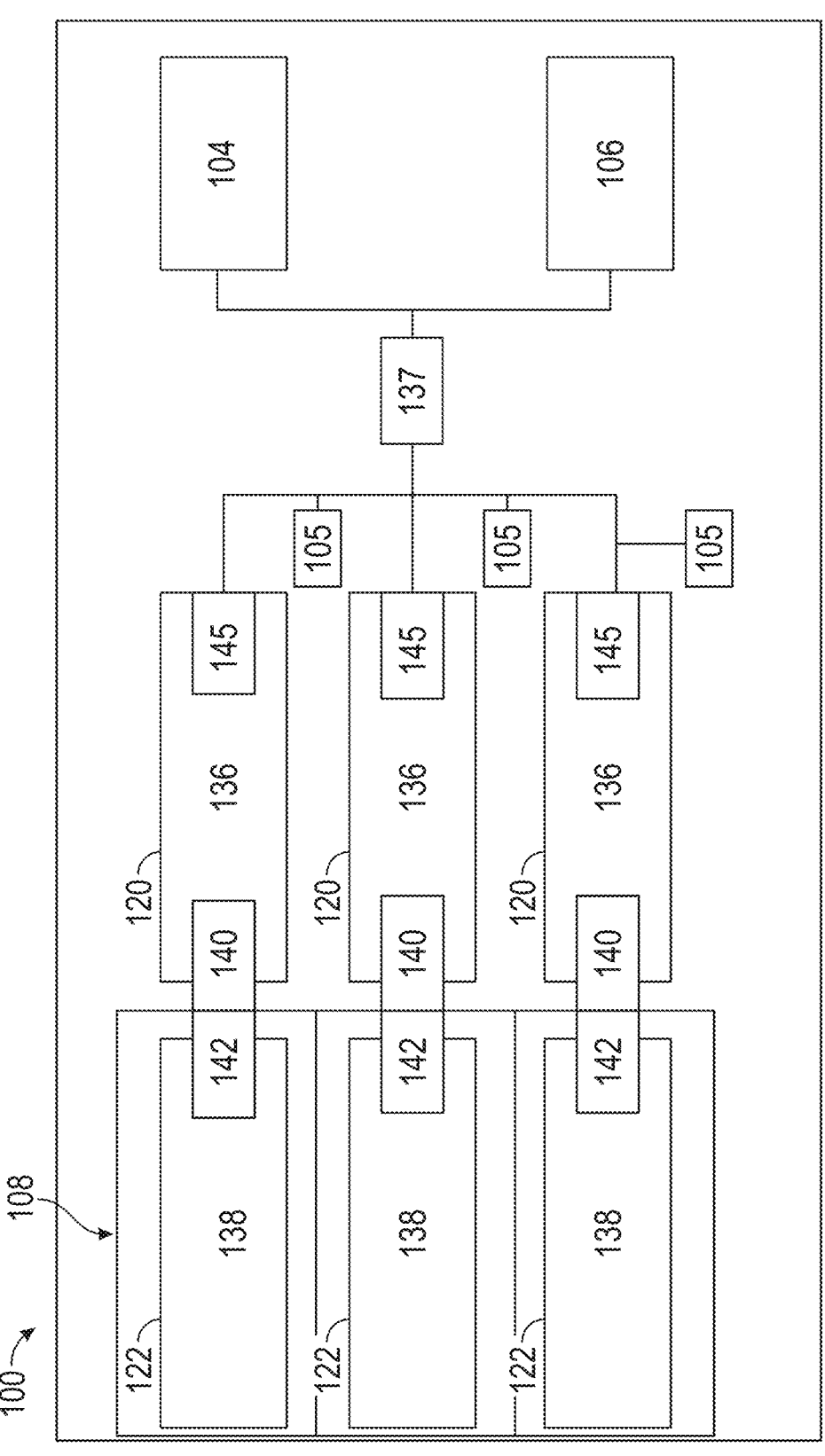
FIG. 5 illustrates a schematic view of a modular medical device platform.

The module lock 120 can include a first electrical connector 136 (FIGS. 2A-2B) and the module connector 122 can include a second electrical connector 138 (FIG. 2C), The first electrical connector 136 can be configured to interface with the second electrical connector 138, such as to establish electrical power or communication connectivity therebetween. For example, the first electrical connector 136 can include a plurality of first mating connectors 140 (FIGS. 2A-2B); and the second electrical connector 138 can include a plurality of second mating connectors 142 (FIG. 2C) each engageable with at least one connector of the plurality of first mating connectors 140. The first electrical connector 136 can be coupled to a wiring harness 137, such as described with regard to FIG. 5 below, positioned within the chassis 102 to establish electrical power of communication connectivity between any of the plurality of controller modules 108 (FIG. 1A) and various electronic or electrical components of the modular medical device platform 100 (FIG. 1A). For example, the plurality of first mating connectors 140 can include a plurality of inputs 145 (FIG. 2B) configured to interface with various connectors or wires of the wiring harness 137 (FIG. 5). In one non-limiting example, each connector of the plurality of first mating connectors 140 can be a male connector and each connector of the plurality of second mating connectors 142 can be a female connector.

In one non-limiting example, the first electrical connector 136 can include a first pin 135 (FIG. 2A) and a first guide 139 (FIG. 2A), and the second electrical connector 138 can include a second pin 141 (FIG. 2C) and a second guide 143 (FIG. 2C). The first guide 139 can be configured to receive the second pin 141 and the second guide 143 can be configured to receive the first pin 135 to help align the plurality of second mating connectors 142 with the plurality of first mating connectors 140, such as during translation of the module connector 122 toward the module lock 120.

The module lock 120 can include a locking mechanism 144. The locking mechanism 144 can include a base plate 146 (FIGS. 2A-2B) and a lock handle assembly 148 (FIGS. 2A-2B). The base plate 146 can extend laterally between the first vertical support member 132 and the second vertical support member 134. The base plate 146 can be fixedly coupled to the first vertical support member 132 and the second vertical support member 134 with various fastening means, such as, but not limited to, one or more bolts, rivets, or welds. The base plate 146 can be configured to support the first electrical connector 136 with respect to the internal frame 130. For example, the plurality of first mating connectors 140 of the first electrical connector 136 can be coupled to the base plate 146 in, for example, but not limited to, a linear arrangement.

The base plate 146 can include a first outer surface 150 (FIG. 2A) and a second outer surface 152 (FIG. 2B). The first outer surface 150 and the second outer surface 152 can extend parallel to each other and orthogonally a front surface 154 (FIG. 2A) of the first vertical support member 132, a front surface 156 (FIG. 2A) of the second vertical support member 134, and the back surface 124 (FIG. 2B) of the drawer enclosure 110. The first outer surface 150 and the second outer surface 152 can extend orthogonally to the back surface 124 of the first controller module 112. The lock handle assembly 148 can include a pair of lock plates 158 (FIG. 2A), a crossbar 160 (FIGS. 2A-2B), and a handle portion 162 (FIGS. 2A-2B). The pair of lock plates 158 can include a first lock plate 164 (FIG. 2A) and a second lock plate 166 (FIG. 2A).

The first lock plate 164 and the second lock plate 166 can be coupled to the base plate 146. For example, the locking mechanism 144 can include a first fastener 168 (FIGS. 2A-2B) and a second fastener 170 (FIG. 2B). The first fastener 168 can extend transversely through the first lock plate 164 into the first outer surface 150 of the base plate 146 and the second fastener 170 can extend transversely through the second lock plate 166 into the second outer surface 152 of the base plate 146. When coupled to the base plate 146, the first lock plate 164 and the second lock plate 166 can extend parallel to and laterally offset from the first outer surface 150 and the second outer surface 152.

The first fastener 168 and the second fastener 170 can be adapted to enable rotation of the first lock plate 164 and the second lock plate 166 relative to the base plate 146. The first fastener 168 and the second fastener 170 can thereby define an axis of rotation A2 (FIG. 2B), or axis of rotation, of the lock handle assembly 148. The crossbar 160 can extend laterally between the first lock plate 164 and the second lock plate 166. For example, the crossbar 160 can be fixedly coupled to an inner surface 172 (FIG. 2A) of the first lock plate 164 and an inner surface 174 (FIG. 2A) of the second lock plate 166. The crossbar 160 can be coupled to the first lock plate 164 and the second lock plate 166 with various fastening means, such as, but not limited to, one or more bolts, rivets, or welds.

The handle portion 162 can be fixedly coupled to the crossbar 160 with various fastening means, such as, but not limited to, one or more bolts, rivets, or welds. The handle portion 162 can extend orthogonally outward from the crossbar 160 toward the access door 126 (FIG. 1A) between the first vertical support member 132 and the second vertical support member 134. The handle portion 162 can form various three-dimensional shapes, such as, but not limited to, a T-shape. In view of the above, a user can depress the handle portion 162 to rotate the lock handle assembly 148 in a clockwise direction around the axis of rotation A2 to move the lock handle assembly into a raised or unlocked position, such as shown in FIG. 2A, or lift the handle portion 162 to rotate the lock handle assembly 148 in a counterclockwise direction around the axis of rotation A2 to move the lock handle assembly 148 into a lowered or unlock position, such as shown in FIG. 2B.

The first lock plate 164 can include a first cam lock 176 (FIG. 2A) and the second lock plate 166 can include a second cam lock 178 (FIG. 2A). The first cam lock 176 can extend outwardly from the inner surface 172 of the first lock plate 164 and the second cam lock 178 can extend outwardly from the inner surface 174 of the second lock plate 166. The first cam lock 176 and the second cam lock 178 can each include a bearing 180 (FIG. 2A) rotationally affixed thereto. The bearing 180 can, for example, but not limited to, a ball bearing, a needle bearing, a bushing, or an outermost surface of the first cam lock 176 or the second cam lock 178. In one non-limiting example, one or more of the first lock plate 164 and the second lock plate 166 can include a detent 182 (FIG. 2B); and one or more of the first outer surface 150 and the second outer surface 152 can each define a recess 184 (FIG. 2B). The recess 184 can be sized and shaped to receive the detent 182. The detent 182 can extend outwardly from at least one of the inner surface 172 of the first lock plate 164 and the inner surface 174 if the second lock plate 166.

The detent 182 and the recess 184 can be adapted to maintain the lock handle assembly 148 in the unlocked position, such as shown in FIG. 2A. For example, a user can depress the handle portion 162 when the lock handle assembly 148 is in the locked position, such as shown in FIG. 2B, to cause the first lock plate 164 and the second lock plate 165 to rotate counterclockwise around the axis of rotation A2 until the detent 182 of one or both of the first lock plate 164 and the second lock plate 166 extends into the recess 184 of one or both of the first lock plate 164 and the second lock plate 166.

The module connector 122 can include a first connector plate 186 (FIG. 2C) and a second connector plate 188 (FIG. 2C). The first connector plate 186 and the second connector plate 188 can be components of the locking mechanism 144. As such, the locking mechanism 144 can be at least partially formed or realized by the module connector 122. The first connector plate 186 and the second connector plate 188 can extend outwardly from the back surface 124 of the drawer enclosure 110 parallel to, and laterally offset from, each other and the first lock plate 164, the second lock plate 166, the first outer surface 150, and the second outer surface 152. The first connector plate 186 can include a first stop 187 (FIGS. 2B-2C) and the second connector plate 188 can include a second stop 189 (FIG. 1B). The first stop 187 and the second stop 189 can generally be projections extending outwardly from the first connector plate 186 and the second connector plate 188. When the lock handle assembly 148 is in the lowered or locked position shown in FIG. 2B, the first lock plate 164 and the second lock plate 165 can rest against the first stop 187 and the second stop 189, respectively. The first connector plate 185 can define a first lock channel 190 (FIG. 2C) and the second connector plate 188 can define a second lock channel 192 (FIG. 2C). The first lock channel 190 and the second lock channel 192 can each include a first surface 194 (FIG. 2C) and a second surface 195 (FIG. 2C) spaced laterally apart from one another to contact and guide the bearing 180 of the first cam lock 176 or the second cam lock 178.

The first lock channel 190 and the second lock channel 192 can be adapted to enable the first cam lock 176 to automatically lock the module connector 122 to the module lock 120 when the drawer enclosure 110 is received within a corresponding rack bay of the plurality of rack bays 115 (FIG. 1A). For example, the first surface 194 and the second surface 196 can be sized and shaped to define a flared opening 197 (FIG. 2C), an angled section 198 (FIG. 2C), and a vertical lock section 199 (FIG. 2C). The flared opening 197 can be adapted to help the bearing 180 of the first cam lock 176 or the second cam lock 178 enter the first lock channel 190 or the second lock channel 192. The vertical lock section 199 can be adapted to limit lateral movement of the bearing 180 of the first cam lock 176 or the second cam lock 178, to thereby prevent the drawer enclosure 110 along the longitudinal axis A1 (FIG. 1A). For example, the vertical lock section 199 can extend orthogonally to the first axis A1.

Figure 3:
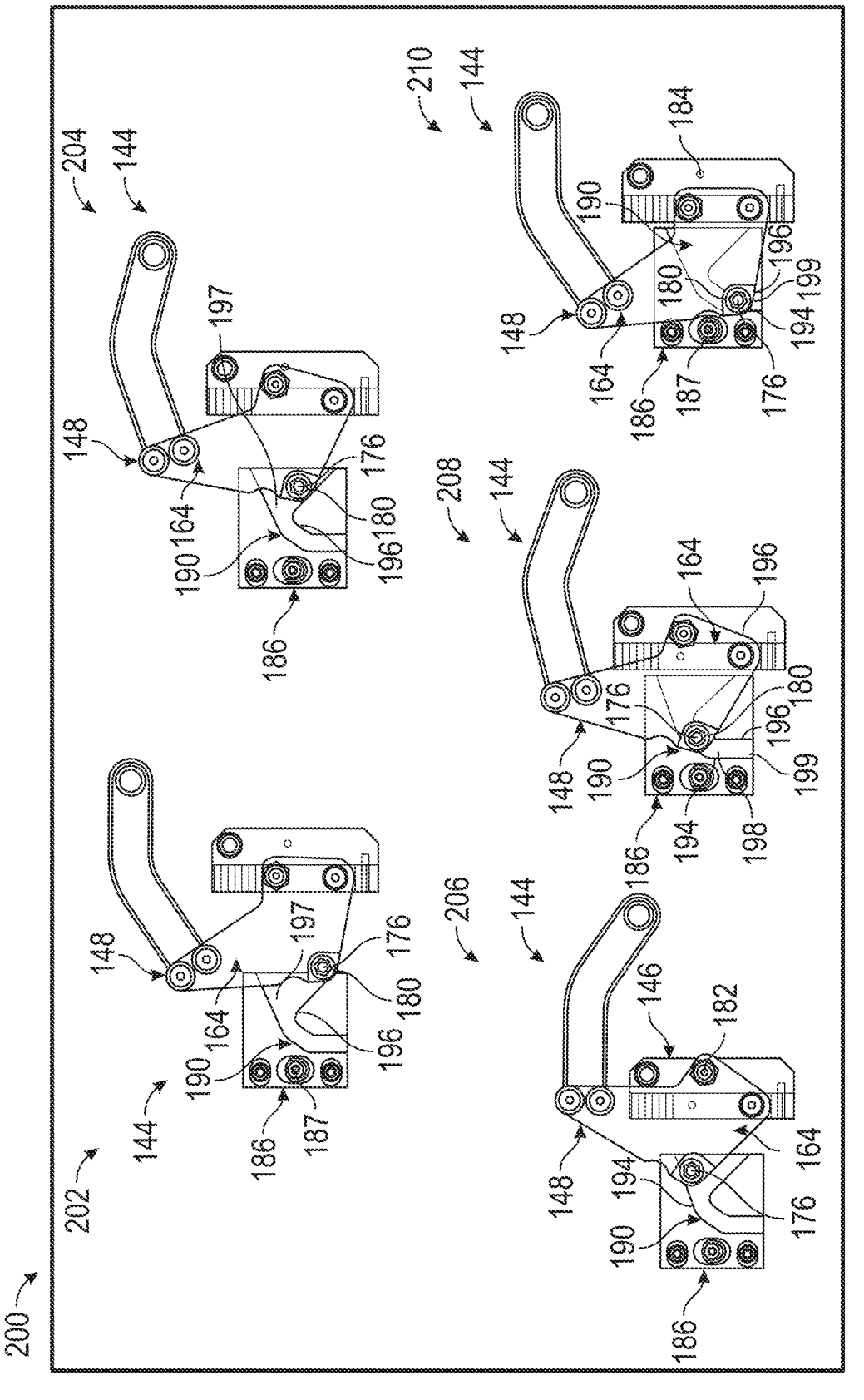
FIGS. 3 illustrates a side view of locking mechanism during various stages of a locking phase.

FIG. 3 illustrates a side view of locking mechanism 144 during various stages of a locking phase 200. FIG. 3 is discussed with reference to the module lock 120 and the module connector 122 shown in FIGS. 1A-2C above. For the sake of brevity, the locking phase 200 is described with reference to the first lock plate 164 (shown in shadow in FIG. 3), the first earn lock 176, the first connector plate 186, and the first lock channel 190. However, it will be appreciated that the following description also applies to the second lock plate 166, the second cam lock 178, the second connector plate 188, and second lock channel 192 shown in FIGS. 2A-2C above. The locking phase 200 occurs during translation of the module connector 122 toward the module lock 120, such when a controller module of the plurality of controller modules 108 (FIG. 1A) is slid into a corresponding rack bay of the plurality of rack bays 115 (FIG. 1A).

In some non-limiting examples, the locking phase 200 can begin at stage 202. During stage 202, the lock handle assembly 148 of the module lock 120 (FIGS. 2A-2B) can begin moving toward the first connector plate 186 of the module connector 122 (FIG. 2C). Eventually, the bearing 180 of the first cam lock 176 will enter the first lock channel 190 by contacting, and rolling along, the second surface 196 within the flared opening 197. During stage 204, the bearing 180 of the first cam lock 176 can continue rolling along the second surface 196 within the flared opening 197 as the locking mechanism 144 moves toward the first connector plate 186. During stages 202 and 204, the second surface 196 within the flared opening 197 can be shaped to cause the lock handle assembly 148 to rotate in clockwise direction around the axis of rotation A2 (FIG. 2A). In other non-limiting examples, the locking phase 200 can be begin at stage 206. During stage 206, the lock handle assembly 148 can begin moving toward the first connector plate 186 until the bearing of 180 of the first cam lock 176 enters the first lock channel 190. In contrast to stage 202, the bearing 180 and the first cam lock 176 can be maintained in a raised position upon entry into the first lock channel 190, such that the first cam lock 176 contacts, and rolls along, the first surface 194 within the flared opening 197. For example, the lock handle assembly 148 can be maintained in the unlocked position shown in FIG. 2A by the detent 182 of the first lock plate 164 and the recess 184 of the base plate 146 as the locking mechanism 144 moves toward the first connector plate 186. Additionally, during stage 206, the first surface 194 within the flared opening 197 can be shaped to cause the detent 182 to disengage the recess 184 (shown in stage 210) and the lock handle assembly 148 of the locking mechanism 144 to begin rotating in counterclockwise direction around the axis of rotation A2.

During stage 208, the bearing 180 of the first cam lock 176 can exit the flared opening 197 and contact and roll along the first surface 194 or the second surface 196 within the angled section 198 as the lock handle assembly 148 continues to move toward the first connector plate 186. The first surface 194 and the second surface 196 within the angled section 198 can be shaped to guide the bearing 180 laterally and downwardly into the vertical lock section 199. Additionally, during stage 208, the lock handle assembly 148 can begin, or continue, rotating in counterclockwise direction around the axis of rotation A2. The locking phase 200 can end during stage 210. During stage 210, the bearing 180 of the first cam lock 176 can contact and roll along the first surface 194 or the second surface 196 within the vertical lock section 199 until the first lock plate 164 contacts the first stop 187 of first connector plate 186 to prevent further movement of the locking mechanism 144 toward the first connector plate 186. When the first lock plate 164 contacts the first stop 187, the lock handle assembly 148 can be in the locked position shown in FIG. 2B, and the first electrical connector 136 (FIG. 2A) and the second electrical connector 138 (FIG. 2C) can be coupled or otherwise engaged with one another to establish power or communication connectivity therebetween.

Figure 4:
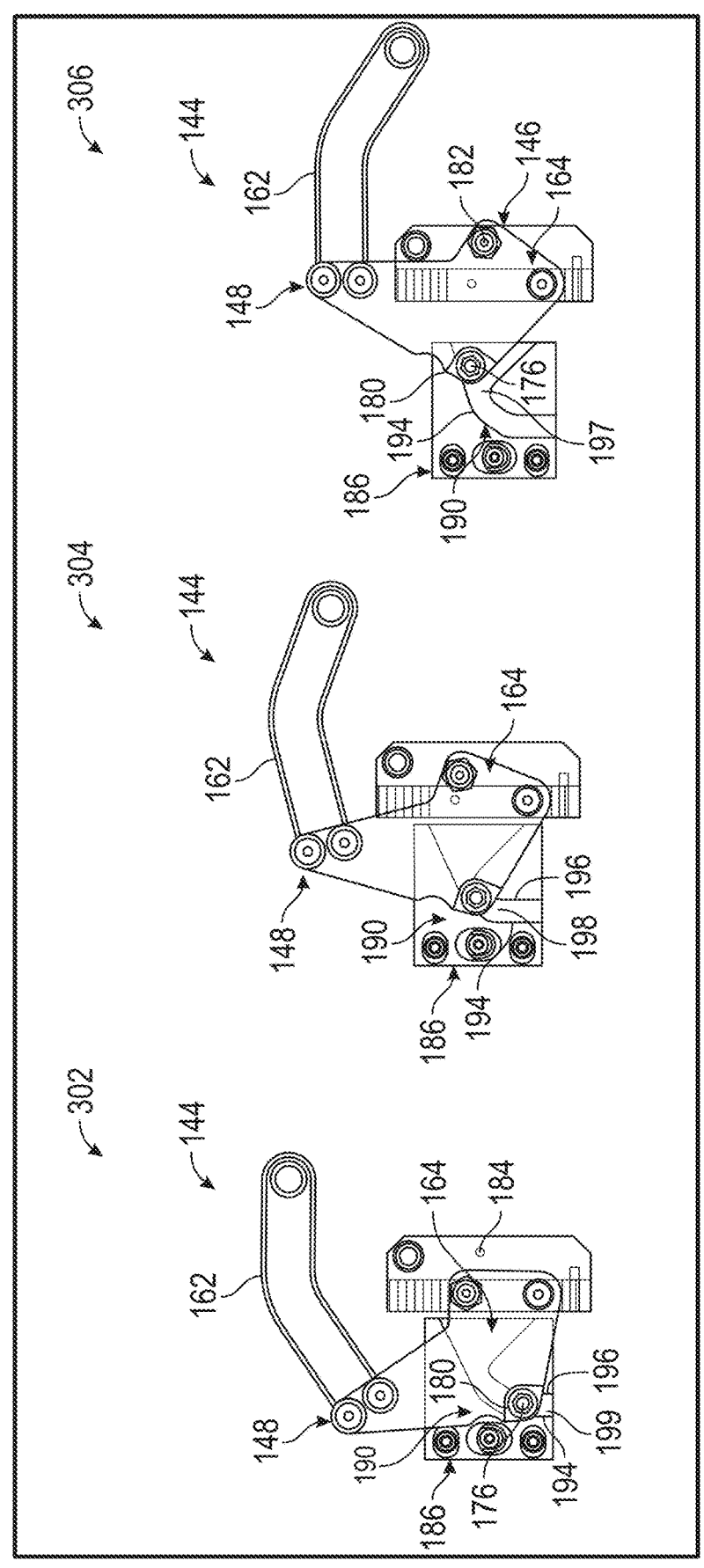
FIG. 4 illustrates a side view of a locking mechanism during various stages of an unlocking phase.

FIG. 4 illustrates a side view of a locking mechanism 144 during various stages of an unlocking phase 300. FIG. 4 is discussed with reference to the module lock 120 and the module connector 122 shown in FIGS. 1A-2C above. For the sake of brevity, FIG. 4 is discussed with reference to the first lock plate 164, the first cam lock 176, the first connector plate 186, and the first lock channel 190. However, it will be appreciated that the following description also applies to the second lock plate 166, the second cam lock 178, the second connector plate 188, and second lock channel 192 shown in FIGS. 2A-2C above. The unlocking phase 300 occurs during clockwise rotation of the lock handle assembly 148 of the locking mechanism 144 around the axis of rotation A2.

The unlocking phase 300 can begin with stage 302. During stage 302, a user can depress the handle portion 162 of the lock handle assembly 148 to begin raising the first cam lock 176 within the first lock channel 190 of the locking mechanism 144, to cause the bearing 180 to roll along the first surface 194 or the second surface 196 within the vertical lock section 199. During stage 304, a user can continue depressing the handle portion 162 of the lock handle assembly 148 to continue raising the first cam lock 176 within the first lock channel 190, to cause the bearing 180 to roll along the first surface 194 or the second surface 196 within the angled section 198. The unlocking phase 300 can end at stage 306. During stage 306, a user can continue depressing the handle portion 162 of the lock handle assembly 148 to cause the bearing 180 to roll along the first surface 194 within the flared opening 197 until the lock handle assembly 148 is in the unlocked position shown in FIG. 2A.

For example, the lock handle assembly can rotate around the axis of rotation A2 until the detent 182 of the first lock plate 164 is received within the recess 184 of the base plate 146. Once the bearing 180 leaves the angled section 198 and enters the flared opening 197, the first cam lock 176 is free to move out of the first lock channel 190. Therefore, a user can then move the module connector 122 away from the module lock 120, such as by sliding a controller module of the plurality of controller modules 108 (FIG. 1A) out of a corresponding rack bay of the plurality of rack bays 115.

FIG. 5 illustrates a schematic view of a modular medical device platform 100. The modular medical device platform can include a wiring harness 137. The wiring harness 137 can be located within the chassis 102 (FIG. 1A). The wiring harness 137 can be adapted to establish electrical power or communication connectivity between any of the plurality of controller modules 108 and various electronic or electrical components of the modular medical device platform 100. For example, the wiring harness 137 can be in electrical communication with the robotic arm 104, the display screen 106, and the second electrical connector 138 of each of the plurality of controller modules 108 via the first electrical connector 136 of each module lock 120, such as by extending between the display screen 106, the robotic arm 104, and the inputs 145 of the first electrical connector 136 of each module lock 120. Accordingly, each of the plurality of controller modules 108 can be in electrical communication with one another and other electronic or electrical components of the modular medical device platform 100 when the plurality of first mating connectors 140 of each first electrical connector 136 and the plurality of second mating connectors 142 of each second electrical connector 138 are connected or otherwise engaged with one another.

In one non-limiting example, the modular medical device platform 100 can include one or more electric motors 105. The one or more electric motors 105 can be configured to electrically implement the unlocking phase 300 shown in FIG. 4 above automatically upon a functional failure of one or more of the plurality of controller modules 108, or in response to one or more user inputs to the display screen 106 or other user-input devices of the modular medical device platform 100, such as including, but not limited to, one or buttons or switches, a mouse, or a keyboard. In such an example, the one or more electric motors 105 can include an electric motor connected to the lock handle assembly 148 (FIG. 4) of each module lock 120 to rotate the lock handle assembly 148 clockwise around the axis of rotation A2 (FIG. 2B) from the locked position shown in stage 302 (FIG. 4) to the unlocked position shown in stage 306 (FIG. 4). In some examples, the one or more electric motors 105 can enable each module lock 120 to omit the handle portion 162 (FIG. 4).

FIG. 6 illustrates a method 400 of replacing one or more controller modules of a modular medical device platform. The steps or operations of the method 400 are illustrated in a particular order for convenience and clarity; many of the discussed operations can be performed by multiple different actors, devices, or systems. It is understood that subsets of the operations discussed in the method 400 can be attributable to a single actor, device, or system and can be considered a separate standalone process or method.

The method 400 can optionally begin with operation 402. The operation 402 can include diagnosing a functional failure of the first controller module by receiving an audible or visual alert generated by the modular medical device platform. For example, the first controller module can be one of a plurality of controller modules of the modular medical device platform, and the modular medical device platform can be configured to generate an audible or visual alert indicative of a failure of one or more internal electronic components of the first controller module. Such an audible or visual alert can be, but is not limited to, a continuous or flashing light emission or audible tone, such as via light emitters or audio drivers present on the first controller module or elsewhere on the modular medical device platform, or a graphical representation or textual description of the functional failure, such as viewable on a display screen of the modular medical device platform.

Alternatively, the operation 402 can include determining a configuration of the first controller module by receiving an audible or visual alert generated by the modular medical device platform. For example, the first controller module can be adapted to enable function of the modular medical device platform used during of one type of surgical procedure, and the replacement controller module can be adapted to enable functions of the modular medical device platform used during a different type of surgical procedure. In such an example, the modular medical device platform can be configured to generate a visual alert indicative of the type of procedure in which the first controller module is adapted to be used. Such a visual alert can be, but is not limited to, a graphical representation or textual description of at least one controller module required to perform a type of surgical procedure, or a graphical representation or textual description or various internal components of the first controller module, such as viewable on a display screen of the modular medical device platform.

The method 400 can include operation 404. The operation 404 can include unlocking a locking mechanism locking a first controller module of the one or more controller modules to a chassis of the modular medical device platform. For example, a user can rotate a lock handle assembly of the locking mechanism in a clockwise direction to cause a first cam lock and a second cam lock to exit a vertical lock and an angle lock section of a first lock channel and a second lock channel, respectively, of the controller module. In one non-limiting example, the operation 402 can include opening an access door of the chassis and depressing a handle portion of the locking mechanism. For example, a user can unlock and open the rear locking door to access the locking mechanism. A user can then depress the handle portion, such as extending toward the access door from within the chassis, to cause the lock handle assembly of the locking mechanism to rotate in a clockwise direction from a locked, or lowered, position to an unlocked, or raised, position.

The method 400 can include operation 406. The operation 406 can include sliding the first controller module out of a rack bay of the chassis of the modular medical device platform. For example, a user can translate the first controller module away from the chassis on a pair of drawer slides coupled to the first controller module and to the chassis within the rack bay. The method 400 can include operation 408. The operation 408 can include decoupling the first controller module from a pair of drawer slides. For example, a user can lift the first controller module from the pair of drawer slides, or remove one or more fasteners securing a pair of flanges of the first controller module to the pair of drawer slides, to decouple the first controller module from the pair of drawer slides.

The method 400 can include operation 410. The operation 410 can include coupling a replacement controller module to the pair of drawer slides. For example, a user can lower the controller module onto the pair of drawer slides, or insert one or more fasteners through a pair of flanges of the replacement controller module and the pair of drawer slides, to couple the replacement controller module to the pair of drawer slides. In some non-limiting examples, the replacement controller module can be similar to the first controller module, such as by being adapted to enable similar functions of the modular medical device platform. In some non-limiting examples, the replacement controller module can be different from the first controller module, such as by being adapted to enable different functions, such as configured for a different surgical procedure relative, of the modular medical device platform.

The method 400 can include operation 412. The operation 412 can include sliding the replacement controller module into the rack bay of the chassis to automatically lock the locking mechanism to operatively couple the replacement controller module to the chassis. For example, a user can translate the replacement controller module toward the chassis on a pair of drawer slides coupled to the replacement controller module and to the chassis within the rack bay until the locking mechanism locks the controller module to the chassis. In one non-limiting example, the operation 410 can include receiving a bearing rotationally affixed to the locking mechanism within a vertical section of a lock channel of the locking mechanism. For example, a user can translate the replacement controller module toward the chassis until a first cam lock and a second cam lock each including a bearing rotationally affixed thereto pass through a flared opening and an angled section of a first lock channel and a second lock channel, respectively, of the locking mechanism.

The foregoing systems and devices, etc. are merely illustrative of the components, interconnections, communications, functions, etc. that can be employed in carrying out examples in accordance with this disclosure. Different types and combinations of sensor or other portable electronics devices, computers including clients and servers, implants, and other systems and devices can be employed in examples according to this disclosure.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided.

Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels; and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure.

This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

EXAMPLES

The following, non-limiting, examples, detail certain aspects of the present subject matter to solve the challenges and provide the benefits discussed herein, among others.

Example 1 is a modular medical device platform comprising: a chassis including a plurality of rack bays, each rack bay of the plurality of rack bays including a pair of drawer slides mounted on opposing sides of the rack bay, the chassis configured to support a medical robot device; a plurality of controller modules, each controller module of the plurality of controller modules including a drawer enclosure including flanges couplable to the pair of drawer slides; and a plurality of module locks affixed to an internal frame of the chassis and aligned with each rack bay of the plurality of rack bays, each module lock of the plurality of module locks including a first electrical connector and a locking mechanism, the locking mechanism including a cam lock adapted to automatically lock a controller module of the plurality of controller modules as the controller module is slid into a rack bay of the plurality of rack on the pair of drawer slides.

In Example 2, the subject matter of Example 1 includes, wherein each controller module of the plurality of controller modules includes a module connector adapted to interface with a corresponding module lock of the plurality of module locks.

In Example 3, the subject matter of Example 2 includes, wherein the module connector includes a lock channel adapted to receive the cam lock within the locking mechanism.

In Example 4, the subject matter of Example 3 includes, wherein the lock channel includes a flared opening to guide the cam lock into the lock channel.

In Example 5, the subject matter of Example 4 includes, wherein the lock channel includes an angled section coupled to the flared opening.

In Example 6, the subject matter of Example 5 includes, wherein the lock channel includes a vertical lock section coupled to the angled section, the vertical lock section adapted to prevent horizontal movement of the controller module when the cam lock is seated within the vertical lock section.

In Example 7, the subject matter of Examples 3-6 includes, wherein the cam lock includes a bearing rotationally affixed to a lock handle assembly of the locking mechanism, the bearing adapted to be received within the lock channel.

In Example 8, the subject matter of Example 7 includes, wherein the lock handle assembly includes a pair of opposing lock plates coupled together by a cross bar.

In Example 9, the subject matter of Example 8 includes, wherein the lock handle assembly includes a handle portion extending from the cross bar toward an access door of the chassis.

In Example 10, the subject matter of Example 9 includes, wherein the handle portion is T-shaped.

In Example 11, the subject matter of Examples 9-10 includes, wherein each lock plate of the pair of opposing lock plates includes a bearing rotationally affixed along an outer corner opposite a pivot point coupled to a vertical support member of the internal frame of the chassis.

In Example 12, the subject matter of Examples 9-11 includes, wherein the module connector includes a pair of lock channels on opposite outer side faces of the module connector to receive the bearing on each lock plate of the pair of opposing lock plates.

In Example 13, the subject matter of Examples 1-12 includes, wherein the chassis includes a locking access door to provide access to the plurality of module locks.

Example 14 is a modular medical device platform comprising: a chassis to support the modular medical device platform, the chassis including an internal support structure comprising a plurality of rack bays; a controller module including a drawer enclosure mountable on drawer slides affixed within a rack bay of the plurality of rack bays, the controller module further including a module connector extending from a back surface of the drawer enclosure; and a module lock affixed on a back portion of the rack bay of the plurality of rack bays, the module lock including a first electrical connector and a cam lock that interfaces with the module connector to electrically couple the controller module to a wiring harness within the chassis and to lock the controller module into the rack bay.

In Example 15, the subject matter of Example 14 includes, wherein the module lock includes a first electrical connector including a plurality of first mating connectors, wherein each of the plurality of first mating connectors provides power or communication connectivity for the controller module.

In Example 16, the subject matter of Example 15 includes, wherein the module connector of the controller module includes a second electrical connector, the second electrical connector including a plurality of second mating connectors adapted to interface with the plurality of first mating connectors of the first electrical connector.

In Example 17, the subject matter of Examples 14-16 includes, wherein the chassis includes a wiring harness communicatively connecting the first electrical connector within the module lock to a robotic arm.

Example 18 is a method of replacing one or more controller modules of a modular medical device platform, the method comprising: unlocking a locking mechanism locking a first controller module of the one or more controller modules to a chassis of the modular medical device platform; sliding the first controller module out of a rack bay of the chassis of the modular medical device platform; decoupling the first controller module from a pair of drawer slides; coupling a replacement controller module to the pair of drawer slides; and sliding the replacement controller module into the rack bay of the chassis to cause the locking mechanism to automatically lock the replacement controller module to the chassis.

In Example 19, the subject matter of Example 18 includes, wherein unlocking the locking mechanism includes opening an access door of the chassis and depressing a handle portion of the locking mechanism; and wherein sliding the replacement controller module into the rack bay includes receiving a bearing rotationally affixed to the locking mechanism within a vertical section of a lock channel of the locking mechanism.

In Example 20, the subject matter of Examples 18-19 includes, wherein the method first comprises diagnosing a functional failure of the first controller module by receiving an audible or visual alert generated by the modular medical device platform.

In Example 21, the subject matter of Example 20 includes, wherein the method first comprises determining a configuration of the first controller module by receiving an audible or visual alert generated by the modular medical device platform.

Example 22 is at least one machine-readable medium including instructions that, when executed by processing circuitry, cause the processing circuitry to perform operations to implement of any of Examples 1-21.

Example 23 is an apparatus comprising means to implement of any of Examples 1-21.

Example 24 is a system to implement of any of Examples 1-21.

Example 25 is a method to implement of any of Examples 1-21.

What is claimed is:

1. A modular medical device platform comprising:
a chassis including a plurality of rack bays, each rack bay of the plurality of rack bays including a pair of drawer slides mounted on opposing sides of the rack bay, the chassis configured to support a medical robot device;
a plurality of controller modules, each controller module of the plurality of controller modules including a drawer enclosure including flanges couplable to the pair of drawer slides; and
a plurality of module locks affixed to an internal frame of the chassis and aligned with each rack bay of the plurality of rack bays, each module lock of the plurality of module locks including a first electrical connector and a locking mechanism, the locking mechanism including a cam lock adapted to automatically lock a controller module of the plurality of controller modules as the controller module is slid into a rack bay of the plurality of rack on the pair of drawer slides,
wherein each controller module of the plurality of controller modules includes a module connector adapted to interface with a corresponding module lock of the plurality of module locks, wherein the module connector includes a lock channel adapted to receive the cam lock within the locking mechanism, wherein the lock channel includes a flared opening and an angled section to guide the cam lock into the lock channel, and wherein the lock channel includes a vertical lock section coupled to the angled section, the vertical lock section adapted to prevent horizontal movement of the controller module when the cam lock is seated within the vertical lock section.

2. The platform of claim 1, wherein the cam lock includes a bearing rotationally affixed to a lock handle assembly of the locking mechanism, the bearing adapted to be received within the lock channel.

3. The platform of claim 2, wherein the lock handle assembly includes a pair of opposing lock plates coupled together by a cross bar.

4. The platform of claim 3, wherein the lock handle assembly includes a handle portion extending from the cross bar toward an access door of the chassis.

5. The platform of claim 4, wherein each lock plate of the pair of opposing lock plates includes a bearing rotationally affixed along an outer corner opposite a pivot point coupled to a vertical support member of the internal frame of the chassis.

6. The platform of claim 5, wherein the module connector includes a pair of lock channels on opposite outer side faces of the module connector to receive the bearing on each lock plate of the pair of opposing lock plates.

7. The platform of claim 1, wherein the chassis includes a locking access door to provide access to the plurality of module locks.

8. A modular medical device platform comprising:

a chassis to support the modular medical device platform, the chassis including an internal support structure comprising a plurality of rack bays;

a controller module including a drawer enclosure mountable on drawer slides affixed within a rack bay of the plurality of rack bays, the controller module further including a module connector extending from a back surface of the drawer enclosure; and a module lock affixed on a back portion of the rack bay of the plurality of rack bays, the module lock including a first electrical connector and a cam lock that interfaces with the module connector to electrically couple the controller module to a wiring harness within the chassis and to lock the controller module into the rack bay, wherein the module connector is adapted to interface with the module lock and the module connector includes a lock channel adapted to receive the cam lock, wherein the lock channel includes a flared opening and an angled section to guide the cam lock into the lock channel, and wherein the lock channel includes a vertical lock section coupled to the angled section, the vertical lock section adapted to prevent horizontal movement of the controller module when the cam lock is seated within the vertical lock section.

9. The platform of claim 8, wherein the module lock includes a first electrical connector including a plurality of first mating connectors, wherein each of the plurality of first mating connectors provides power or communication connectivity for the controller module.

10. The platform of claim 9, wherein the module connector of the controller module includes a second electrical connector, the second electrical connector including a plurality of second mating connectors adapted to interface with the plurality of first mating connectors of the first electrical connector.

11. The platform of claim 8, wherein the chassis includes a wiring harness communicatively connecting the first electrical connector within the module lock to a robotic arm.

* * * * *